United States Patent [19]

Beyer

[11] 4,370,495
[45] Jan. 25, 1983

[54] PROCESS FOR THE PREPARATION OF α-[4-(4-CHLOROBENZOYLAMINOETHYL)-PHENOXY]-ISOBUTYRIC ACID

[75] Inventor: Peter Beyer, Mannheim-Wallstadt, Fed. Rep. of Germany

[73] Assignee: Boehringer Mannheim GmbH, Mannheim, Fed. Rep. of Germany

[21] Appl. No.: 30,798

[22] Filed: Apr. 17, 1979

[30] Foreign Application Priority Data

May 12, 1978 [DE] Fed. Rep. of Germany ....... 2820759

[51] Int. Cl.³ ............................................ C07C 99/00
[52] U.S. Cl. .................................................. 562/451
[58] Field of Search ....................... 562/451, 469, 471; 560/42; 424/319

[56] References Cited

U.S. PATENT DOCUMENTS 3,781,328 12/1973 Witte et al. ............................ 560/42
3,948,973 4/1976 Phillips ................................. 562/469
3,970,694 7/1976 Minai et al. .......................... 562/469

FOREIGN PATENT DOCUMENTS 2153348 5/1972 Fed. Rep. of Germany ........ 560/42
2356655 5/1974 Fed. Rep. of Germany ...... 562/469

OTHER PUBLICATIONS

Hebron, Chem. Abst., vol. 87, #134684f, (1977).
Mievillo, Chem. Abst., vol. 85, #192382a, (1976).

Primary Examiner—James H. Reamer
Attorney, Agent, or Firm—Felfe & Lynch

[57] ABSTRACT

A process for the preparation of 2-[4-(4-chlorobenzoylaminoethyl)-phenoxy]-2-methylpropionic acid of the formula

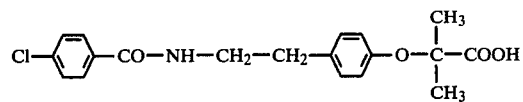

which process comprises reacting N-(4-chlorobenzoyl)-tyramine with acetone and chloroform in a mole ratio of 1:20–100:2–10, in the presence of 3 to 4 moles of alkali per mole of chloroform, at a temperature of from about 10° to 40° C.

6 Claims, No Drawings

PROCESS FOR THE PREPARATION OF α-[4-(4-CHLOROBENZOYLAMINOETHYL)-PHENOXY]-ISOBUTYRIC ACID

The present invention is concerned with a process for the preparation of α-[4-(4-chlorobenzoylaminoethyl)-phenoxy]-isobutyric acid, as well as of its pharmacologically acceptable salts.

α-[4-(4-Chlorobenzoylaminoethyl)-phenoxy]-isobutyric acid, which can also be called 2-[4-(4-chlorobenzoylaminoethyl)-phenoxy]-2-methylpropionic acid, is a compound of the formula:

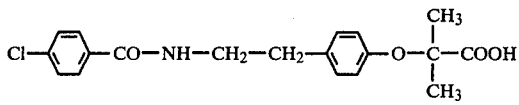

This compound possesses very valuable therapeutic properties: it has a lipid- and cholesterol-lowering action and is far superior to the known compound clofibrate.

In the case of the previously described process for the preparation of this compound, given in German Patent Specification No. 21 49 070, tyramine is reacted with 4-chlorobenzoyl chloride to give the corresponding di-(4-chlorobenzoyl) compound which is saponified with an aqueous solution of potassium hydroxide in methanol to give N-(4-chlorobenzoyl)-tyramine which, in turn, is reacted with an appropriate reactive carboxylic acid or with an ester thereof.

The reactive carboxylic acid compound which can be usefully used is, for example, α-bromoisobutyric acid or an ester thereof. However, this process suffers from the disadvantage that α-bromoisobutyric acid and the esters thereof are relatively expensive. Furthermore, a long reaction time between the phenol and the α-bromoisobutyric acid or ester thereof of about 70 hours is necessary, as well as a high actual running time and a high consumption of energy.

In the case of the preferred reaction with α-bromoisobutyric acid or an ester thereof, an intermediate is obtained which is difficult to purify and in the case of working up, residues of the poisonous α-bromoisobutyric acid have to be removed which gives rise to problems for reasons of protection of the environment and also because of its lachrymatory action. The intermediate must be hydrolyzed, involving the use of organic solvents as solubilizing agents, and additional energy costs arise. Since, to a large extent, the acid end product is contaminated with the starting phenol, the acid must, in addition, be separated from the phenol by means of sodium carbonate.

It is an object of the present invention to modify the above-mentioned known process for the preparation of α-[4-(4-chlorobenzoylaminoethyl)-phenoxy]-isobutyric acid in such a manner that it can be carried out at a low ambient temperature and, nevertheless, leads to high yields and to a pure product and thus is more economic than the conventional process and employs reaction components which are as compatible with the environment as possible and are also inexpensive.

Surprisingly, this object is achieved by not using the reactive carboxylic acid component as such but rather by allowing it to be formed intermediately by reacting N-(4-chlorobenzoyl)-tyramine with acetone and chloroform in the presence of an alkali.

Thus, according to the present invention, there is provided a process for the preparation of 2-[4-(4-chlorobenzoylaminoethyl)-phenoxy]-2-methylpropionic acid, wherein 1 mole N-(4-chlorobenzoyl)-tyramine is reacted with 20 to 100 mole acetone, 2 to 10 and preferably 3 to 6 mole chloroform and 3 to 4 and preferably 3.2 to 3.5 mole of alkali per mole of chloroform at a temperature of from about 10° to 40° C., preferably of from 15° to 30° C. and more preferably of 20° to 25° C., whereafter, if desired, the acid obtained is salified with a non-toxic organic or inorganic base.

The alkali used is preferably sodium or potassium hydroxide or carbonate.

The excess of acetone used simultaneously serves as a solvent.

The preparation of the reactive carboxylic acid components is described by Ch. Weizmann et al., in J.A.C.S., 70, 1153/1948 and by A. Merz et al., in Chem. Ber., 110, 96. As described in the paper by A. Merz et al., in Chem. Ber., 110, page 96 and especially pages 99 and 100, at about 56° C. there is formed from acetone and chloroform in an alkaline medium, a mixture of α-hydroxyisobutyric acid (yield 55%), methacrylic acid (about 10%) and only a small amount of α-chloroisobutyric acid. Since α-hydroxyisobutyric acid and methacrylic acid do not react with the phenol in the desired manner, it was surprising that, in the case of the reaction conditions according to the present invention, the desired end product, 2-[4-(4-chlorobenzoylaminoethyl)-phenoxy]-isobutyric acid, is formed in a yield which is increased by more than 20% and at most by more than 40% of theory, in comparison with the previously used process. It is, therefore, to be assumed that, under these conditions, the α-chloroisobutyric acid or correspondingly reacting intermediate stages, such as 2,2-dichloro-3,3-dimethyloxirane and 2-oxo-3,3-dimethyloxirane, are formed as labile intermediate stages in substantially higher concentration than was to have been expected from the above-mentioned literature references.

All the starting materials used in the process according to the present invention are cheaper than those previously used. The reaction time is substantially shorter and is, at most, 2 hours at reflux temperature, apart from which the supply of energy is not necessary. The desired end product is formed immediately and is easily purified. In the working up of the reaction mixture, only relatively harmless by-products, such as hydroxyisobutyric acid, have to be removed.

The following Example is given for the purpose of illustrating the present invention:

EXAMPLE

N-(4-Chlorobenzoyl)-tyramine

A solution of 205.5 g. (1.5 mole) tyramine in 2.25 liters water containing 310 g. (7.75 mole) sodium hydroxide is treated with 5 g. active charcoal, cooled to 5° C., mixed within the course of about 40 minutes with 600 g. (3.428 mole) 4-chlorobenzoyl chloride at 5° C., with good stirring, and subsequently stirred for 15 minutes at 5° C. Thereafter, stirring is continued for 2 hours without external cooling, the internal temperature thereby slowly increasing to about 28° C. After the addition of 4.5 liters methanol, the reaction mixture is stirred for 3 hours at an external temperature of 55° C.

The reaction solution is then left to stand overnight at ambient temperature, subsequently cooled to 5° C., adjusted to pH 4.3 to 4.5 with about 350 ml. concentrated hydrochloric acid at 5° to 10° C. and then stirred for 15 minutes. N-(4-Chlorobenzoyl)-tyramine precipitates out in admixture with 4-chlorobenzoic acid. The precipitate is filtered off with suction and then washed portionwise with 800 ml. water. The moist residue is introduced into 6 liters saturated aqueous sodium bicarbonate solution and subsequently stirred for 3 hours at ambient temperature. The solid product is then filtered off with suction, washed portionwise with 800 ml. water and dried overnight at 60° C. in an air-circulating drying cabinet. The yield of crude N-(4-chlorobenzoyl)-tyramine is 358 g. (87% of theory, referred to the amount of tyramine used); m.p. 168°/170°-172° C. By recrystallization from 1750 ml. ethanol, there are obtained 314 g. N-(4-chlorobenzoyl)-tyramine (76% of theory, referred to the tyramine); m.p. 170°/171°-172° C. From the mother liquor, by concentration to a volume of about 300 ml., there are obtained a further 23 g. N-(4-chlorobenzoyl)-tyramine (5.6% of theory, referred to the tyramine); m.p. 166°/166°-170° C.

Recovery of 4-chlorobenzoic acid

From the mother liquor, after stirring with sodium carbonate, there is obtained, by acidification with concentrated hydrochloric acid to pH 1-2, suction filtration and washing three times with 300 ml. amounts of water, followed by drying in an air-circulating drying cabinet at 60° C., 4-chlorobenzoic acid in a yield of 318 g. (59.5% of theory, referred to the amount of 4-chlorobenzoyl chloride used); m.p. 234°/235°-236° C.

2-[4-(p-Chlorobenzoylaminoethyl)-phenoxy]-2-methylpropionic acid

Variant 1.

560 g. (14 mole) Pulverized sodium hydroxide are added to a suspension of 265 g. (0.961 mole) N-(4-chlorobenzoyl)-tyramine in 4.6 liters acetone at an internal temperature of 10° to 15° C., the internal temperature thereby increasing to 25° to 28° C. Subsequently, 520 g. (4.356 mole) chloroform are added dropwise in the course of 4 hours in such a manner that, with simultaneously external cooling with running water, an internal temperature of 35° to 37° C. is maintained. The reaction mixture is further stirred for 30 minutes at 35° to 37° C., then heated under reflux for 2.5 hours and subsequently left to stand overnight at ambient temperature.

The acetone is distilled off as far as possible at water-pump vacuum and the slurry-like residue is mixed at ambient temperature with 8.7 liters water, well stirred for 15 minutes, mixed with 600 ml. acetone and the pH adjusted to 3.5 with 350 ml. semi-concentrated hydrochloric acid at about 20° C., followed by stirring for 3 hours at ambient temperature. The precipitate is filtered off with suction, washed portionwise with 1.2 liters water, pasted in a water-moist state with 250 ml. acetone, filtered off with suction and washed portionwise with 250 ml. acetone on the suction filter. After drying in an air-circulating drying cabinet at 70° C., there are obtained 314 g. (90.3% of theory; referred to the N-(4chlorobenzoyl)-tyramine) of crude end product; m.p. 177°/178°-180° C. In the thin layer chromatogram, in addition to 0.5% N-(4-chlorobenzoyl)-tyramine, one or two very weak impurities are also detected. By recrystallization from 5.5 liters acetone, the hot acetone solution thereby being treated with 10 g. of active charcoal, there are obtained, after suction filtration, portionwise washing with 150 ml. ice-cold acetone and drying overnight in an air-circulating drying cabinet at 70° C., 237.2 g. (68.2% of theory, referred to the N-(4-chlorobenzoyl)-tyramine) of the desired product; m.p. 182°/183°-184° C.

By concentrating the recrystallization mother liquor to a volume of about 800 ml. and cooling in an ice-bath, there is obtained a further yield of 62 g. 2-[4-(p-chlorobenzoylaminoethyl)-phenoxy]-2-methylpropionic acid (17.8% of theory, referred to N-(4-chlorobenzoyl)-tyramine); m.p. 180°-182° C.

2-[4-(p-Chlorobenzoylaminoethyl)-phenoxy]-2-methylpropionic acid

Variant 2. (reaction at 20°-25° C.)

184 g. (4.6 mole) Pulverized sodium hydroxide are added while stirring and in the course of 5 minutes to a suspension of 72 g. (0.262 mole) N-(4-chlorobenzoyl)-tyramine in 1.76 liters acetone with external cooling with an ice-bath, at an internal temperature of 10° C.; the internal temperature can thereby increase to a maximum of 21° C. Subsequently, 171.6 g. (1.44 mole) chloroform are added dropwise within the course of 4 hours at an internal temperature of 20° to at most 25° C. During the addition of the chloroform, cooling is initially carried out with running water and, after about 1.5 hours, with ice water. After about 2 hours, the reaction mixture becomes viscous during the addition of the chloroform and relatively difficult to stir. It is preferable to employ a strong stirrer mechanism made of V$_4$A steel in order, on the one hand, to be able to stir well when the reaction mixture becomes very viscous and, on the other hand, to provide for a good removal of heat and a good mixing of the reaction components during the course of the addition of the remainder of the chloroform. After the addition of all of the chloroform, the reaction mixture is stirred overnight while cooling with running water, the internal temperature thereby dropping to 15° C. (temperature recorder). Subsequently, the remainder of the unreacted acetone is substantially completely distilled off at water pump vacuum and at a maximum bath temperature of 25° C. and the residue is vigorously stirred with 750 ml. toluene and then filtered with suction. The residue is washed portionwise with 250 ml. toluene and subsequently suspended, in a still moist state, in 3 liters water. The suspension is then adjusted to a pH of 1 with about 138 ml. semi-concentrated hydrochloric acid and thereafter stirred for 1 hour at ambient temperature. Subsequently, the product is filtered off with suction, washed twice with 50 ml. amounts of water and dried overnight in an air-circulating drying cabinet at 60° C. There are obtained 87 g. 2-[4-(p-chlorobenzoylaminoethyl)-phenoxy]-2-methylpropionic acid, which corresponds to 91.5% of theory, referred to the N-(4-chlorobenzoyl)-tyramine; m.p. 178°-180° C.

2-[4-(p-Chlorobenzoylaminoethyl)-phenoxy]-2-methylpropionic acid

Variant 3. (reaction at 16°-19° C.)

At this temperature, the desired product is obtained in a yield of 81.4% of theory.

The reaction can, of course, also be carried out at temperatures which are lower than 10° C. In the case of a reaction temperature of 0° C., the reaction is incomplete and in the crude product obtained, in addition to 50 to 70% of the desired product, there can also be detected about 30 to 40% N-(4-chlorobenzoyl)-tyramine by thin layer chromatography.

It will be understood that the specification and examples are illustrative but not limitative of the present invention and that other embodiments within the spirit and scope of the invention will suggest themselves to those skilled in the art.

What is claimed is:

1. In a process for the preparation of 2-[4-(4-chlorobenzoylaminoethyl)-phenoxy]-2-methylpropionic acid of the formula

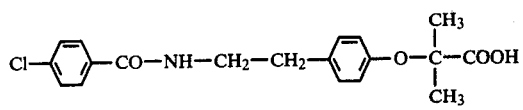

comprising reacting N-(4-chlorobenzoyl)-tyramine with acetone and chloroform, the improvement consisting of carrying out the reaction at a temperature of from about 20° to 40° C. in a mole ratio of 1:20–100:2–10 (tyramine:acetone:chloroform), and in the presence of 3 to 4 moles of alkali per mole of chloroform.

2. Improvement as claimed in claim 1 wherein the reaction product obtained is neutralized with a non-toxic organic or inorganic base to produce a salt of said 2-[4-(4-chlorobenzoylaminoethyl)-phenoxy]-2-methylpropionic acid.

3. Improvement as claimed in claim 1 wherein 3 to 6 moles of chloroform are used per 1 mole of N-(4-chlorobenzoyl)-tyramine.

4. Improvement as claimed in claim 1 wherein 3.2 to 3.5 moles of alkali are used per mole of chloroform.

5. Improvement as claimed in claim 1 wherein the reaction is carried out at a temperature of 15° to 30° C.

6. Improvement as claimed in claim 5 wherein the reaction is carried out at a temperature of 20° to 25° C.

* * * * *